United States Patent [19]

Vinnars

[11] Patent Number: 5,310,768

[45] Date of Patent: May 10, 1994

[54] METHOD FOR IMPROVING THE GLUTAMINE CONTENT IN SKELETAL MUSCLE AND COMPOSITION THEREFORE

[75] Inventor: Erik Vinnars, Stockholm, Sweden

[73] Assignee: AB Erik Vinnars, Stockholm, Sweden

[21] Appl. No.: 895,997

[22] Filed: Jun. 11, 1992

Related U.S. Application Data

[63] Continuation-in-part of Ser. No. 784,127, Oct. 29, 1991, abandoned.

[30] Foreign Application Priority Data

Oct. 29, 1987 [SE] Sweden ............................. 04217/87

[51] Int. Cl.$^5$ .................... A61K 31/19; A61K 31/195
[52] U.S. Cl. .................................... 514/574; 514/557; 514/561
[58] Field of Search ............... 514/574, 561, 400, 419, 514/423, 562, 564, 565, 566

[56] References Cited

U.S. PATENT DOCUMENTS

| | | | |
|---|---|---|---|
| 3,542,929 | 11/1970 | Roberts | 514/574 |
| 4,663,166 | 5/1987 | Veech | 514/561 |
| 4,929,449 | 5/1990 | Veech | 514/561 |
| 5,100,677 | 3/1992 | Veech | 514/561 |

FOREIGN PATENT DOCUMENTS 564922 12/1984 Australia .
0146474 7/1985 European Pat. Off. .
8701589 3/1987 European Pat. Off. .
8703806 7/1987 PCT Int'l Appl. .

OTHER PUBLICATIONS

Hammerqvist, F., et al., "Alpha-ketoglutarate preserves protein synthesis and free glutamine in skeletal muscle after surgery", *Surgery* (1991), vol. 109, pp. 28-36.

Wernerman, J., et al., "Alpha-ketoglutarate and postoperative muscle catabolism", *The Lancet* (1990), vol. 335, pp. 701-703.

Dialog 05710808, Medline 86011808, "Changes in protein metabolism in cachexia and catabolism" (1985).

The Merk Index, 10th Edition (1983), p. 762, cite #5140.

*Primary Examiner*—Frederick E. Waddell
*Assistant Examiner*—Raymond J. Henley, III
*Attorney, Agent, or Firm*—Beveridge, DeGrandi, Weilacher & Young

[57] ABSTRACT

A method of treatment of postoperative and posttraumatic patients for improving the glutamine content in skeletal muscle by administrating alpha-ketoglutarate; also, a composition for carrying out the method.

7 Claims, 1 Drawing Sheet

METHOD FOR IMPROVING THE GLUTAMINE CONTENT IN SKELETAL MUSCLE AND COMPOSITION THEREFORE

REFERENCE TO A RELATED APPLICATION

The present application is a continuation-in-part of U.S. Pat. application Ser. No. 07/784,127, filed on Oct. 29, 1991, now abandoned, which is incorporated by reference in its entirety.

INTRODUCTION AND BACKGROUND

The present invention relates to a method of treatment of postoperative and posttraumatic patients for improving the glutamine content in skeletal muscle by administrating alpha-ketoglutarate. The invention also relates to a composition for carrying out the method.

In states of illness, surgical operations and injuries, profound changes are induced in the energy and protein metabolism of the human body. This means, for example, loss of active cellular mass, leading to muscular fatigue, pronounced apathy and loss of appetite, and a period of convalescence involving general weariness which, for instance after a biliary tract operation, may last 5-6 weeks before the patient has regained his normal function. The cellular mass which is broken down very rapidly in different states of illness will need a time for reestablishment which is about four times as long as the time of breakdown for the same mass.

In severe states of illness and injuries, and in postoperative states, parenteral nutritional support is generally applied. In the past, preparations for intravenous nutritional support generally contained an aqueous solution of a high caloric content carbohydrate, such as glucose and the like, and electrolytes. In prolonged states of illness or in injuries and surgical operations, the nitrogen balance of the body must however be considered, i.e. the ratio of nitrogen loss to nitrogen intake. In the case of negative nitrogen balance, the parenteral nutritional support can be supplemented with an amino acid supply in an attempt to improve the nitrogen balance. Different amino acid compositions for parenteral supply are previously known, see e.g. SE Patent Application 8203965-2 and DE-A 25 30 246 concerning amino acid nutrient compositions in renal failure, WO 82/00411 concerning a nutrient composition containing branched-chain amino acids, and WO 83/03969 concerning an aqueous nutrient solution consisting of L-amino acids.

From a survey made of the free amino acid pattern in the muscles, it has been found that skeletal muscle, which is the major body tissue in respect of weight, has a free amino acid pool of which 62% consists of glutamine (see Bergstroem et al., "Intracellular free amino acid concentrations in human muscle tissue", J. of Appl. Physiol., Vol 36, No 6, 1974). In states of illness, injuries or surgical operations, this content decreases by at lest 50% and, in states of blood poisoning, even more (see Vinnars et al., "Influence of the postoperative state on the intracellular free amino acids in human muscle tissue", Annals of Surg., Vol 182, 6:665-671, 1975).

It has been found that this glutamine reduction cannot be affected by enteral or parenteral nutritional support according to the methods hitherto available (see Vinnars et al., "Metabolic effects of four intravenous nutritional regiments in patients undergoing elective surgery. 11. Muscle amino acids and energy rich phosphates", Clin. Nutr., 2:3-11, 1983). There is probably a correlation between the inability immediately postoperatively to make a negative nitrogen balance positive, the inability to normalize the exhausted intracellular glutamine pool, and the reduced muscular strength. This reduction probably depends on a reduced protein synthesis capacity postraumatically in skeletal muscle (see Wernerman et al., "Protein syntheses after trauma as studied by muscle ribosome profiles", Proceedings in the 7th ESPEN Congress. ED. Dietze et al, Karger, Basel).

The addition to the nutritional support of a dipeptide of the type ornithine-alpha-ketoglutarate to a commercial amino acid solution has been found to improve to some extent, but not to normalize, the intracellular glutamine pool (see Leander et al., "Nitrogen sparing effect of Ornicetil in the immediate postoperative state", Clin. Nutr. 4:43-51, 1985). However, this preparation is very expensive and it has not been possible so far to evaluate whether its use in parenteral nutrition confers a clinical advantage.

Postoperatively, the patient often exhibits loss of appetite, making it difficult to supply nutrition, although there are possibilities, by tube-feeding, of supplying different kinds of nutrient solutions. Since most patients do not tolerate this way of feeding, it becomes necessary to resort to intravenous feeding. The nutrition substrates available for energy metabolism are various sugar solutions and fatty emulsions, which today seem appropriate. However, the amino acid solutions available are inadequate, both because it is not possible to add tyrosine in sufficient amounts since this is a relatively insoluble amino acid, and because certain important amide derivatives of amino acids (e.g., glutamine and asparagine) cannot be included. This is due to difficulties in heat-sterilizing solutions of such amides, and also to the fact that the amides are unstable when stored. Another problem is that these compounds are relatively sparingly soluble and therefore require large amounts of water when being prepared.

After elective surgery, for instance biliary tract operations, it has been found that the negative nitrogen balance primarily depends on reduced protein synthesis which is assessed by determining the ribosome activity in skeletal muscle (see Wernerman et al., "Protein synthesis in skeletal muscle after abdominal surgery: The effect of total parenteral nutrition", JPEN, 1985). An increased protein breakdown occurs only in very severe traumas and primarily in septic states. This reduced protein synthesis capacity cannot be affected by conventional intravenous or enteral nutritional support.

SUMMARY OF THE INVENTION

It has now been demonstrated for the first time that the addition of alpha-ketoglutarate, alone or in combination with conventional amino acid solutions, to a parenteral nutrition program can prevent such reduction of the protein synthesis capacity and, hence, also improve the nitrogen balance and even make it positive. The abnormal intracellular amino acid pattern in skeletal muscle, and especially the 50% reduction of the glutamine pool involved, can then be partially prevented.

Thus one object of the present invention is to provide a method of treatment of postoperative and posttraumatic patients for improving the glutamine content in skeletal muscle which comprises administrating alpha-ketoglutarate.

Alpha-ketoglutarate may be added alone or in combination with a conventional amino acid solution (known in the art), optionally with the addition of L-glutamine or analogous thereof, L-asparagine and/or acetoacetate, glucose and/or fat.

The present invention also relates to a composition for treatment of postoperative and posttraumatic patients for improving the glutamine content in skeletal muscle, said composition comprising a conventional amino acid mixture and alpha-ketoglutarate in an amount sufficient to give a concentration of alpha-ketoglutarate of at least 0.1 g/kg body weight/day.

Optionally, the composition may further comprise L-glutamine or analogs thereof, L-asparagine or its keto derivative, acetoacetate, glucose and/or fat.

DETAILED DESCRIPTION OF THE INVENTION

Figure 1:
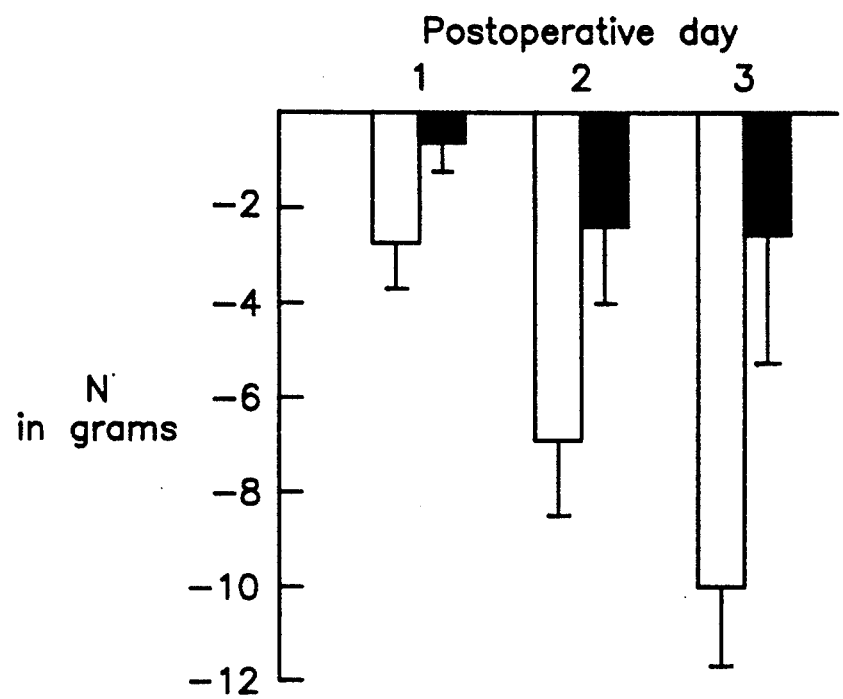

Preliminary tests on patients subjected to a biliary tract operation have shown that an addition of alpha-ketoglutarate to a conventional parenteral nutritional support program improves the nitrogen balance of the patients and hence also their recovery to a great extent. Furthermore, the pathological amino acid changes which normally occur after injury or surgical operation are normalized and, also, the reduction of the ribosome activity is prevented. This is the first time it has been possible more specifically to act on the negative effects of injury or surgical operation on the protein metabolism.

If the components which should be added to a conventional parenteral support cannot be sterilized in solution, they can be brought into form suitable for administration by sterile filtration of an aqueous solution, followed by rapid cooling and cold storage limited to a few months. One alternative is freeze-drying the sterile-filtered solution, yielding a sterile powder. Immediately before administration, this powder can be added to a conventional amino acid mixture. Also other forms of powder sterilization known in the art, not relying on heat, are possible. The possibility of using the Na salt of the compounds in order to increase the solubility has also been considered.

The concentration of at least 0.1 g/kg body weight/day corresponds to at least 9 g component/l aqueous solution if an 1 l amino acid solution/day is given to a patient weighing 70 kg. One example of a conventional amino acid solution expressed in g dry component/l aqueous solution is:

| | |
|---|---|
| glycine | 1–12 |
| aspartate | 1–10 |
| glutamate | 2–12 |
| alanine | 2–20 |
| arginine | 2–14 |
| cysteine/cystine | 0.4–2.0 |
| histidine | 2–8 |
| isoleucine | 2–8 |
| leucine | 2–8 |
| lysine | 2–12 |
| methionine | 1–6 |
| phenylalanine | 4–10 |
| proline | 4–10 |
| serine | 2–10 |
| threonine | 2–8 |
| tryptophan | 1–3 |
| tyrosine | 0.2–1 |
| valine | 2–8 | and optionally 5–30 g/l L-glutamine and/or 0.5–10 g/l L-asparagine and/or 0.5–10 g/l acetoacetate, or salts or esters thereof.

A preferred amount of L-glutamine in the composition of the present invention is 10–30 g/l and an especially preferred amount is 15–25 g/l, specifically 20 g/l. A preferred amount of alpha-ketoglutarate in the composition of the present invention is 10–25 g/l specifically 16.5 g/l.

In therapeutic tests, preferred compositions have included the following suitable components (expressed in g dry component/l aqueous solution):

| Example | 1 | 2 | 3 | 4 | 5 |
|---|---|---|---|---|---|
| glycine | 5.9 | 5.9 | 5.9 | 5.9 | 5.9 |
| aspartate | 4.8 | 4.8 | 4.8 | 4.8 | 4.8 |
| glutamate | 6.8 | 6.8 | 6.8 | 6.8 | 6.8 |
| alanine | 12 | 12 | 12 | 12 | 12 |
| arginine | 8.4 | 8.4 | 8.4 | 8.4 | 8.4 |
| cysteine/cystine | 0.42 | 0.42 | 0.42 | 0.42 | 0.42 |
| histidine | 5.1 | 5.1 | 5.1 | 5.1 | 5.1 |
| isoleucine | 4.2 | 4.2 | 4.2 | 4.2 | 4.2 |
| leucine | 5.9 | 5.9 | 5.9 | 5.9 | 5.9 |
| lysine | 6.8 | 6.8 | 6.8 | 6.8 | 6.8 |
| methionine | 4.2 | 4.2 | 4.2 | 4.2 | 4.2 |
| phenylalanine | 5.9 | 5.9 | 5.9 | 5.9 | 5.9 |
| proline | 8.0 | 8.0 | 8.0 | 8.0 | 8.0 |
| serine | 6.0 | 6.0 | 6.0 | 6.0 | 6.0 |
| threonine | 4.2 | 4.2 | 4.2 | 4.2 | 4.2 |
| tryptophan | 1.4 | 1.4 | 1.4 | 1.4 | 1.4 |
| tyrosine | 0.4 | 0.4 | 0.4 | 0.4 | 0.4 |
| valine | 5.5 | 5.5 | 5.5 | 5.5 | 5.5 |
| L-glutamine | 20 | — | 10 | 10 | 10 |
| alpha-ketoglutarate | — | 16.5 | 10 | 10 | 10 |
| asparagine | — | — | — | 2 | 4 |
| acetoacetate | — | — | — | 2 | — |

When alpha-ketoglutarate should be included in the composition, it must be added in the form of its sodium salt or its esters since it is otherwise extremely sparingly soluble. Glutamine can also be added in the form of the sodium salt thereof, thus improving its solubility.

When preparing a composition including alpha-ketoglutarate, heat sterilization can be used if the components are not heat sensitive. When including heat sensitive components, such as L-glutamine, they can be dissolved in sterile pyrogen-free water at 30°–50° C. The solution is sterile-filtered and rapidly cooled and may thereafter be stored for a few months in a solution in a cooled state or for an even longer time in the frozen state, or stored after freeze-drying for several years in sterile powder form, until it should be used together with an amino acid solution of conventional commercial type, for instance of the VAMIN ® type (amino acid nutrient composition from KabiVitrum AB). Carbohydrates and fatty substances can also be added to the infusion solution. When using alpha-ketoglutarate, it must be added in the form of its sodium salt or its esters, which is also possible, but not necessary, in the case of L-glutamine.

A newly prepared composition as above, either in large bags or in separate vials for each substrate, is then administered to patients exhibiting disordered nitrogen balance, resulting either from a surgical operation or from an injury or illness, the administration being conducted during a period of from 2–4 days to several weeks or until the patient can start eating ordinary food, with a dosage of 20–170 kJ/kg body weight/day, including 0.1–0.2 g amino acid nitrogen/kg body weight/day.

EXAMPLE 1

In a study of patients who had been subjected to a biliary tract operation, the patients were divided into a test group of 8 persons and a control group of 9 persons.

All patients were subjected to a parenteral nutritional treatment program (TPN) with an intake of intravenous liquids of 35 ml/kg body weight/day and an energy intake corresponding to 135 kJ/kg body weight/day in the form of equal parts of fat (Intralipid 20%, KabiVitrum) and carbohydrate (Glukos 10%, Pharmacia Infusion). The control group was given 0.2 g amino acid nitrogen/kg body weight/day in the form of VAMIN ® (KabiVitrum). The test group was also given 0.136 g alpha-ketoglutarate ($\alpha$-KG)/kg body weight/day (i.e. 9.52 g/l solution). Thus, both groups were given isonitrogenous and isocaloric amounts of amino acid and energy. Electrolytes, trace metals and vitamins were administered to both groups.

The daily nitrogen balance in means ±SEM was as follows:

|  | Day 1 | Day 2 | Day 3 | cum. NB |
|---|---|---|---|---|
| $\alpha$-KG | −0.54 ± 0.53 | −1.65 ± 1.86 | −0.15 ± 1.07 | −2.33 ± 1.30 |
| Control | −3.64 ± 0.64 | −2.83 ± 0.86 | −3.16 ± 0.70 | −9.57 ± 1.30 |
| Significance | **($p < 0.01$) | | *($p < 0.05$) | *($p < 0.05$) |

(cum. NB = cumulative nitrogen balance)

The glutamine concentration (in mole/kg wet weight) in skeletal muscle was affected in the following manner:

|  | Preoperatively | 3rd postoperative day | Δ |
|---|---|---|---|
| $\alpha$-KG | 15.42 ± 0.79 | 11.75 ± 0.87 | −3.67 ± 0.49 |
|  |  | $p < 0.05$ |  |
| Control | 14.58 ± 1.39 | 8.71 ± 0.83 | −5.87 ± 0.91 |

The present amino acid nutrient compositions thus have a very favorable effect on postoperative and posttraumatic states since they provide an improved nitrogen balance and unaltered protein synthesis capacity and, hence, promote a considerably quicker and improved recovery of patients than is the case of previously known amino acid nutrient compositions.

EXAMPLE 2

Metabolically healthy patients (n=21) undergoing elective cholecystectomy, as a model of surgical trauma, participated in the study. The characteristics of the patients and the operative procedure are presented in Table I. TPN (total parenteral nutrition) was given for 3 days after elective cholecystectomy. The patients received isocaloric (135 kJ/kg body weight/24 h) and isonitrogenous (0.2 g of nitrogen/kg body weight/24 h) nutrition (Table II). In one group (n=9) $\alpha$-KG, 0.194/g/kg body weight/24 h (13.58 g/l solution) was added; the other group (n=12) served as controls. A conventional amino acid solution (VAMIN ®; KabiVitrum, Stockholm, Sweden), not including glutamine, was given to both groups. The nonprotein calories were provided as equal amounts of glucose (Glukos 20%, Pharmacia Infusion, Uppsala, Sweden) and fat (Intralipid 20%; KabiVitrum). The extra caloric supply in the form of AKG was negligible and therefore not taken into account. On the day of surgery the administration of TPN was started after the operation and amounted to only half that given on the following day.

TABLE I

Characteristics of the patients and the operative procedure

|  | Control | AKG |
|---|---|---|
| Men/women (n) | 6/6 | 3/6 |
| Age (year) | 52 ± 3 | 43 ± 4 |
| Weight (kg) | 75 ± 4 | 72 ± 5 |
| Height (cm) | 172 ± 2 | 170 ± 3 |
| Inoperative blood loss (ml) | 280 ± 70 | 270 ± 70 |
| Operating time (min) | 102 ± 15 | 115 ± 15 |

Data are expressed as mean ± SEM.

TABLE 2

Content in the isocaloric and isonitrogenous TPN given to the control and AKG groups, respectively, after cholecystectomy.

|  | Control | AKG |
|---|---|---|
| Energy (kJ) | 135 | 135 |
| Total nitrogen (mg) | 200 | 200 |
| Nonessential amino acids (mg) | 830 | 830 |
| Essential amino acids (mg) | 645 | 645 |
| AKG (mg) | — | 194 |

Nutrients are expressed in per kg body weight per 24 h.

Tissue specimens for ribosome and amino acid analysis were obtained by the percutaneous needle biopsy technique from the lateral portion of the musculus quadriceps femoris approximately 15 cm above the knee. Biopsies were performed before the operation, immediately after induction of anesthesia, and on the morning of the third postoperative day after local anesthetization of the skin. Specimens of 50 to 60 mg wet weight were used for ribosome determination, 20 to 30 mg wet weight for amino acid analysis, and 15 to 20 mg wet weight to assess the chloride and water content of the skeletal muscle tissue. The specimens used for ribosome and amino acid analyses were frozen in liquid nitrogen within 3 minutes and stored at −80° C. until analyzed. The ribosome analysis was performed within 2 weeks. The specimens for amino acid determination were stored for no longer than 3 months before analysis. Occasionally there were difficulties in obtaining adequate amounts of biopsy material on the third postoperative day. Hence the two groups were extended to include eight subjects on whom the muscle amino acid concentration determination and the ribosome analysis were performed.

The method for analyzing the concentration and size distribution of ribosomes in skeletal muscle has been describe in detail elsewhere.

The concentration of free amino acids in skeletal muscle tissue and plasma was determined by ion-exchange chromatography with an automated amino acid analyzer (Alpha Plus; LKB, Bromma, Sweden) employing DC-6 ion-exchange resin (Benson; Durrum Instrument Corp., Sunnyvale, Calif.) and lithium citrate buffers. The muscle specimens were homogenized manually in a glass homogenizer. The proteins were precipitated in sulfosalicylic acid. The concentrations of the free intracellular amino acids in skeletal muscle were expressed per liter of intracellular water. The calculation of the water content and the distribution of the extracellular and intracellular volumes were based on Nernst's equation, taking into account the total water and chloride content of the muscle specimen, as well as the total protein and chloride concentration in serum. The chloride content of the muscle specimens was determined by potentiometric titration. Because the chloride ion is freely diffusible across the cell membrane, its equilibration between the extracellular and intracellular space is constant (26:1), assuming the membrane potential to be normal (i.e. −87.2 mV).

Urine was collected in 24 hours portions. The urinary nitrogen content was determined by a chemiluminescent nitrogen system (771C pyroreactor, 720C nitrogen detector; Antek Instruments, Inc. Houston, Texas). The nonurinary nitrogen losses were estimated to be 1.5 g per 24 h, which was added to the urinary nitrogen losses in each subject.

PROTEIN SYNTHESIS IN SKELETAL MUSCLE

In the control group the total ribosome concentration per mg of DNA in skeletal muscle decreased by 17.8%±3.2% (p<0.001) on the third postoperative day compared with the preoperative levels of 100%. No significant change was seen in the AKG group. In the control group the percentage of polyribosomes out of total ribosomes decreased significantly (p<0.01) on the third day after surgery compared with preoperative levels. In contrast, no significant changes were observed in the AKG group. The concentration of polyribosomes per mg of DNA in skeletal muscle was calculated by multiplying the total ribosome concentration per mg of DNA by the relative percentage of polyribosomes out of total ribosomes for every individual subject. On the third postoperative day the concentration of polyribosomes in the control group decreased by 25.8%±4.5% (p<0.001) compared with the values of 100% obtained before surgery. In the AKG group the concentration remained unchanged and was significantly higher (p<0.05) than that noted in the control group 3 days after surgery.

Nitrogen Balance and Description of FIG. 1

In FIG. 1 is shown the cumulative nitrogen balance in grams of nitrogen on days 1 to 3 after elective cholecystectomy. Two groups of patients received either conventional TPN (n=12; open bars) or TPN with an addition of AKG (n=9; filled bars). The cumulative nitrogen balance during the 3 days immediately after surgery was negative (−9.9±1.8 g; p<0.001) in the control group, whereas it remained at equilibrium in the AKG group. The cumulative nitrogen balance was improved (p<0.05) in the AKG group compared with the control group. The serum urea values were within the normal limits every day after surgery, and no alterations were observed in any subject studied. Values are given in means ± SEM.

Jeppson et al. (*Am. J. Physiol.*, 1988, 255, E166-172) has shown a connection between the protein synthesis and glutamine level in skeletal muscle. This connection is of importance for the interpretation of the results given in the examples.

The treatment with alpha-ketoglutarate prevents a lowering of glutamine level in skeletal muscle and at the same time prevents a lowering of the ribosome concentration. The protein synthesis capacity has thus been shown to be maintained in the skeletal muscle for the postoperative patients treated with alpha-ketoglutarate.

By preserving the lean body mass of the patients they are less susceptible to complications after the operation and can recover faster from convalescence.

Further variations and modifications of the foregoing will be apparent to those skilled in the art and such variations and modifications are attended to be encompassed by the claims that are appended hereto.

I claim:

1. A method of treatment of postoperative and posttraumatic patients for improving the glutamine content in skeletal muscle, said method comprising intravenous administration to a patient in need thereof of a solution comprising alpha-ketoglutarate as the sole active agent for improving said glutamine content, wherein said alpha-ketoglutarate is administered in an amount sufficient to at least partially prevent reduction of said glutamine content in said patients and with the proviso that said solution excludes glutamine.

2. The method according to claim 1, wherein said solution further comprises an amino acid solution.

3. The method according to claim 1, wherein said solution further comprises L-asparagine and/or acetoacetate.

4. The method according to claim 1, wherein said solution further comprises glucose and/or fat.

5. The method according to claim 1, wherein said amount is an amount sufficient to produce a concentration of said alpha-ketoglutarate of at least 0.1 g/kg body weight/day.

6. The method according to claim 1, wherein said solution further comprises L-asparagine and/or acetoacetate, glucose and/or fat.

7. A method of treatment of postoperative and posttraumatic patients for improving the glutamine content in skeletal muscle, said method comprising intravenous administration to a patient in need thereof of a solution consisting essentially of an amino acid mixture, with the proviso that said solution excludes glutamine, and alpha-ketoglutarate as the sole active agent for improving said glutamine content and optionally glucose and/or fat, wherein said alpha-ketoglutarate is administered in an amount sufficient to at least partially prevent reduction of said glutamine content in said patients.

* * * * *